US006384299B1

(12) United States Patent
Gutiérrezi-Armenta et al.

(10) Patent No.: US 6,384,299 B1
(45) Date of Patent: May 7, 2002

(54) PLANT RETINOBLASTOMA-ASSOCIATED GENE

(75) Inventors: Cristano Gutiérrezi-Armenta; Andres Pelayo Sanz-Burgos; Qi Xie, all of Madrid (ES); Paula Suarez Lopez, Norwich (GB)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 09/213,293

(22) Filed: Dec. 14, 1998

Related U.S. Application Data

(63) Continuation of application No. PCT/EP97/03070, filed on Jun. 12, 1997.

(30) Foreign Application Priority Data

Jun. 13, 1996 (WO) .............................. PCT/ES96/600130

(51) Int. Cl.[7] .......................... C12N 5/04; C12N 15/29; C12N 15/82; C12N 15/87
(52) U.S. Cl. .................... 800/279; 435/320.1; 435/419; 536/23.6; 800/298
(58) Field of Search ............................ 435/69.1, 320.1, 435/410, 419, 468, 412; 536/23.6, 24.5; 800/278, 279, 285, 286, 290, 295, 298, 301, 320.1

(56) References Cited

FOREIGN PATENT DOCUMENTS

| WO | 92 05272 A | 2/1992 | ............ C12P/21/06 |
|----|-----------|--------|-----------------------|
| WO | 92/05272  | * 4/1992 | ............ C12P/12/06 |
| WO | 95 06661  | 3/1995 | .......... C07H/21/104 |
| WO | 95/06661  | * 3/1995 | ............ C07H/21/04 |
| WO | 95 07708 A | 3/1995 | ........... A61K/38/17 |
| WO | 95/07708  | * 3/1995 | ........... A61K/38/17 |

OTHER PUBLICATIONS

"Reintroduction of a Normal Retinoblastoma Gene into Retinoblasoma and Osteosarcoma cells Inhibits the Replication Associated Function of SV40 Large T Antigen" Uzvolgyi et al, Cell Growth & Differentiation (Jun. 1991), vol. 2, pp. 297–303.
Shen et al, "Partial sequencing and mapping of clones . . . ," Plant Molecular Biology, vol. 26, pp. 1085–1101 (1994).*
Abstract, No. XP002042537, "Zea mays retinoblastomalike protein (ZmRB) mRNA, partial cds.; and Grafi et al, " A Maize cDNA Encoding a Member of the Retinoblastoma Protein.*
Qian et al, "Biological Function of the Retinoblastoma Protein . . . ," Molecular and Cellular Biology, vol. 12, No. 12, pp. 5363–5372 (1992).*
Xie et al, "Identification and analysis of a retinoblastoma binding motif . . . " The Embo Journal, vol. 14, No. 16, pp. 4073–4082 (1995).*
Collin et al, "The Two Nonstructural Proteins from Wheat Dwarf Virus . . . ," Virology, vol. 219, pp. 324–329. (1996).*
Soni et al, "A Family of Cyclin D. Homologs from Plants Differentially . . . ," The Plant Cell, vol. 7, pp. 85–103 (1995).*
Xie et al, "Plant cells contain a novel member of the retinoblastoma family of growth . . . ," The Embo Journal, vol. 15, No. 18, pp. 4900–4908 (1996).*
Grafi et al, "A maize cDNA encoding a member of the . . . ," Proc. Natl. Acad. Sci USA, vol. 93, pp. 8962–8967 (1996).*
Dahl et al, "The D–Type Alfalfa Cyclin Gene cycMs4 . . . ," Plant Cell, vol. 7, pp. 1847–1857 (1995).*
Shen B. et al.: "Partial Sequencing and mapping of clones form two Cdna libraires" Plant Molecule Biology, vol. 26, No. 4, Nov. 1994, pp. 1085–1101, XP002042536 see whole document & AC T18395 Embl Database, Apr. 23, 1994, Heidelberg, see whole document.
Grafi B. et al.: "AC U52099" Embl Database, Apr. 26, 1996, Heidelberg, XP002042537 see whole document.
Qian Y et al: Biological Function of the Retinoblastoma Protein Requires Distinct Domains for Hyperohosphorylation and Transcritption Factor Binding Molecular and Cellular Biology, vol. 12, No. 12, pp. 5363–5372, XP000615356 see whole document.
Xie Q. et al.: "Identification and analysis of a retinoblastoma binding motif in the replication protein of plant DNA virus: requirement for efficient viral replication" The Embo Journal, vol. 14, No. 16, Aug. 15, 1995, pp. 4073–4082, XP002042538 cited in the application see whole document, esp. pp. 4079/80.
Collins S. et al.: "The two nonstructural proteins from wheat dwarf virus involved in viral gene expression and replication are retinoblastoma–binding proteins" Virology, vol. 219, No. 1, May 1, 1996, pp. 324–329, XP002042539 see whole document, esp. p. 325 right col.
Soni R. et al: "A family of cyclin D homologs from plants differentially controlled by growth regulators and containing the conserved retinoblastoma protein interaction motif" The Plant Cell, vol. 85–103, XP002042540 cited the whole document, esp. p. 97, right col.

(List continued on next page.)

Primary Examiner—Amy J. Nelson
Assistant Examiner—Ashwin D. Mehta
(74) Attorney, Agent, or Firm—Nixon & Vanderhye

(57) ABSTRACT

The present invention is based on the isolation and characterization of a plant cell DNA sequence encoding for a retinoblastoma protein. Such finding is based on the structural and functional properties of the plant retinoblastoma protein as possible regulator of the cellular cycle, of the cellular growth and of the plant cellular differentiation. For this reason, among other aspects, it is claimed the use of retinoblastoma protein or the DNA sequence which encodes for it in the growing control of vegetable cells, plants and/or vegetable virus, as well as the use of vectors, cells, plants or animals, or animal cells modified through the manipulation of the control route based on plant retinoblastoma protein.

6 Claims, 3 Drawing Sheets

OTHER PUBLICATIONS

Wie Q. et al.: "Plants cells contain a novel member of the retinoblastoma family of growth regulatory proteins" The Embo Journal, vo. 15, No. 18, Sep. 16, 1996, pp. 4900–4908, XP002042541 see whole document.

Grafi G. et al.: "A maize cDNA encoding a member of the retinoblastoma protein family: involvment in endoreduplication" PMAS, U.S.A., vol. 93, No. 17, Aug. 20, 1996 pp. 8962–8967, XP002042542 see whole document.

* cited by examiner

Pocket B

| | | | | | | | | | | |
|---|---|---|---|---|---|---|---|---|---|---|
| Maize Rb1 | 405 | NEKCADVTIH | IFFSKILKLA | AIRIRNICER | VQC..VEQTE | RVTNVFKQII | EQQTTLFFNR | HIDDEILCCL | YGVARVCQLE | LTFREILNNY | 492 |
| Xenopus Rb | 614 | QQKSTSLS.. | LFYKKVYLIA | YKRLESSICSS | LLSDHPELEQ | VIWTLLQHTI | QQEYELMRDR | HLDQIMMCSM | YGICKAKNID | LRFKTIVTAY | 701 |
| Chicken Rb | 630 | QKPQKSTSLS | LFYKKVFRLA | YLRLFTEFFR | LLSEHPDLEP | IIWTLFQHTL | QNESELMRDR | HLDQIMMCSM | YGICKVKNVP | LRFKTIVSAY | 719 |
| Mouse Rb | 632 | QKPLKSTSLA | LFYKKVYRLA | YLRLNTLCAR | LLSEHPELEH | IIWTLFQHTL | QNEYELMRDR | HLDQIMMCSM | YGICKVKNID | LKFKIIVTAY | 721 |
| Human Rb | 639 | QKPLKSTSLS | LFYKKVYRLA | YLRLNTLCER | LLSEHPELEH | IIWTLFQHTL | QNEYELMRDR | HLDQIMMCSM | YGICKVKNID | LKFKIIVTAY | 728 |
| Human p107 | 780 | NRPKRTGSLA | LFYKKVYHLA | SVRLRDLCLK | LDVSN.ELRR | KIWTCFEFTL | VHCPDLMKDR | HLDQLLLCAF | YIMAKVTKEE | RTFQEIMKSY | 868 |
| Human p130 | 828 | NRPRKTSSLS | LFFRKVYHLA | AVRLRDLCAK | LDISD.ELRK | KIWTCFEFSI | IQCPELMRDR | HLDQLMCAI | YVMAKVTKED | KSEQNIMRCL | 916 |

| | | | | | | | | | |
|---|---|---|---|---|---|---|---|---|---|
| | 493 | REAQCKPEV | FSSTYI. | .......... | .......... | .......... | .......... | ...GSTNRNG | VLVSRHVGII | 525 |
| | 702 | KGLTNTNQET | FKHVLIR. | .......... | .......... | .......... | .......... | .......... | .DGQHDSII | 726 |
| | 720 | KELPNTNQET | FKRVLIR. | .......... | .......... | .......... | .......... | .......... | EEQYDSII | 744 |
| | 722 | KDLPHAAQET | FKRVMIR. | .......... | .......... | .......... | .......... | .......... | EEEFDSII | 746 |
| | 729 | KDLPHAVQET | FKRVMLIK. | .......... | .......... | .......... | .......... | .......... | ..EEYDSII | 753 |
| | 869 | RNQPQANSHV | YRSVLLK.. | .......SIP | REVVAYNKNI | NDDFEMID.. | .......... | ....CDLED | ATKTPDCSSG | PVKEERSDLI | 931 |
| | 917 | ETQPQARSQV | YRSVIIKGKR | KRRNSGSSDS | RSHQNSPTEL | NKDRTSRDSS | PVMRSSSTLP | VPQPSSAPPT | PTRLTGANSD | MEEEERGGLI | 1006 |

| | | | |
|---|---|---|---|
| | 526 | TFINEVFNPA | AMPFLV | 541 |
| | 727 | VFVNLVFMQK | LKSHIL | 742 |
| | 745 | VFVNLVFMQK | LKTNIL | 760 |
| | 747 | VGVNSVFMQR | LKTNIL | 762 |
| | 754 | VFVNSVFMQR | LKTNIL | 769 |
| | 869 | KFVNIIVNGR | VKSFAL | 947 |
| | 1007 | QFVANIVIKQ | IKTFAM | 1002 |

*Fig. 1A*

PLANT RETINOBLASTOMA-ASSOCIATED GENE

This application is a continuation of PCT Application No. PCT/EP97/03070, filed Jun. 12, 1997.

The present invention relates the proteins having biological activity in plant and animal systems, to polynucleotides encoding for the expression of such proteins, to oligonucleotides for use in identifying and synthesizing these proteins and polynucleotides, to vectors and cells containing the polynucleotides in recombinant form and to plants and animals comprising these, and to the use of the proteins and polynucleotides and fragments thereof in the control of plant growth and plant vulnerability to viruses.

BACKGROUND OF THE INVENTION

Cell cycle progression is regulated by positive and negative effectors. Among the latter, the product of the retinoblastoma susceptibility gene (Rb) controls the passage of mammalian cells through G1 phase. In mammalian cells, Rb regulates G1/S transit by inhibiting the function of the E2F family of transcription factors, known to interact with sequences in the promoter region of genes required for cellular DNA replication (see eg Weinberg, R. A. Cell 81,323 (1995); Nevins, J. R. Science 258,424 (1992)). DNA tumor viruses that infect animal cells express oncoproteins that interact with the Rb protein via a LXCXE motif, disrupting Rb-E2F complexes and driving cells into S-phase (Weinberg ibid; Ludlow, J. W. FASEB J. 7, 866 (1993); Moran, E. FASEB J. 7, 880 (1993); Vousden, K. FASEB J. 7, 872 (1993)).

The present inventors have shown that efficient replication of a plant geminivirus requires the integrity of an LXCXE amino acid motif in the viral RepA protein and that RepA can interact with members of the human Rb family in yeast (Xie, Q., Suárez-López, P. and Gutiérrez, C. EMBO J. 14, 4073 (1995). The presence of the LXCXE motif in plant D-type cyclins has also been reported (Soni, R., Carmichael, J. P., Shah, Z. H. and Murray, J. A. H. Plant Cell 7, 85–103 (1995)).

SUMMARY OF THE INVENTION

The present inventors have now identified characteristic sequences of plant Rb proteins and corresponding encoding polynucleotides for the first time, isolated such a protein and polynucleotide, and particularly have identified sequences that distinguish it from known animal Rb protein sequences. The inventors have determined that a known DNA sequence from the maize encoding a vegetable Rb plant protein and is hereinafter called ZmRb1. ZmRb1 has been demonstrated by the inventors to interact in yeasts with RepA, a plant geminivirus protein containing LXCXE motif essential for its function. The inventors have further determined that geminivirus DNA replication is reduced in plant cells transfected with plasmids encoding either ZmRb1 or human p130, a member of the human Rb family.

Significantly the inventors work suggests that plant and animal cells may share fundamentally similar strategies for growth control, and thus human as well as plant Rb protein such as ZmRb1 will be expected to have utility in, inter alia, plant therapeutics, diagnostics, growth control or investigations and many such plant proteins will have similar utility in animals.

In a first aspect of the present invention there is provided the use of retinoblastoma protein in controlling the growth of plant cells and/or plant viruses. Particularly, the present invention provides control of viral infection and/or growth in plant cells wherein the virus requires the integrity of an LXCXE amino acid motif in one of its proteins, particularly, e. g., in the viral RepA protein, for normal reproduction. Particular plant viruses so controlled are Geminiviruses.

A preferred method of control using such proteins involves applying these to the plant cell, either directly or by introduction of DNA or RNA encoding for their expression into the plant cell which it is desired to treat. By over expressing the retinoblastoma protein, or expressing an Rb protein or peptide fragment thereof that interacts with the LXCXE motif of the virus but does not affect the normal functioning of the cell, it is possible to inhibit normal virus growth and thus also to produce infection spreading from that cell to its neighbors.

Alternatively, by means of introducing anti-sense DNA or RNA in plant cells in vectors form that contain the necessary promoters for the DNA or RNA transcription, it will be possible to exploit the well known anti-sense mechanism in order to inhibit the expression of the Rb protein, and thus the S-phase. Such plants will be of use, among other aspects to replicate DNA or RNA until high levels, e.g. in yeasts. The methods to introduce anti-sense DNA in cells are very well known for those skilled in the art: see for example "Principles of gene manipulation—An introduction to Genetic Engineering (1994) R. W. Old & S. B. Primrose; Oxford-Blackwell Scientific Publications Fifth Edition p398.

In a second aspect of the present invention there is provided recombinant nucleic acid, particularly in the form of DNA or cRNA (mRNA), encoding for expression of Rb protein that is characteristic of plants. This nucleic acid is characterised by one or more characteristic regions that differ from known animal Rb protein nucleic acid and is exemplified herein by SEQ ID No 1, bases 31-2079.

The DNA or RNA can have a sequence that contains the degenerated substitution in the nucleotides of the codons in SEQ ID No. 1, and in where the RNA the T is U. The most preferred DNA or RNA are capable of hybridate with the polynucleotide of the SEQ ID No. 1 in conditions of low stringency, preferably being the hybridization produced in conditions of high stringency.

The expressions "conditions of low stringency" and "conditions of high stringency" are understood by those skilled, but are conveniently exemplified in U.S. Pat. No. 5,202,257, Col-9-Col 10. If some modifications were made to lead to the expression of a protein with different amino acids, preferably of the same kind of the corresponding amino acids to the SEQ ID No 1; that is, are conservative substitutions. Such substitutions are known by those skilled, for example, see U.S. Pat. No. 5,380,712, and it is only contemplated when the protein has activity with retinoblastoma protein.

Preferred DNA or CRNA encodes for a plant Rb protein having A and B pocket sub-domains having between 30% and 75% homology with human Rb protein, particularly as compared with p130, more preferably from 50% to 64% homology. Particularly the plant Rb protein so encoded has the C706 amino acid of human Rb conserved. Preferably the spacer sequence between the A and B pockets is not conserved with respect to animal Rb proteins, preferably being less than 50% homologous to the same region as found in such animal proteins. Most preferably the protein so encoded has 80% or more homology with that of SEQ NO 2 of the sequence listing attached hereto, still more preferably 90% or more and most preferably 95% or more. Particularly provided is recombinant DNA of SEQ ID No 1 bases 31 to 2079, or the entire SEQ ID No 1, or corresponding RNAS, encoding for maize CDNA clone encoding ZmRb1 of SQ ID No 2.

In a third aspect of the present invention there is provided the protein expressed by the recombinant DNA or RNA of the second aspect, novel proteins derived from such DNA or RNA, and protein derived from naturally occurring DNA or RNA by mutagenic means such as use of mutagenic PCR primers.

In a fourth aspect there are provided vectors, cells and plants and animals comprising the recombinant DNA or RNA of correct sense or anti-sense, of the invention.

In a particularly preferred use of the first aspect there is provided a method of controlling cell or viral growth comprising administering the DNA, RNA or protein of the second or third aspects to the cell. Such administration may be direct in the case of proteins or may involve indirect means, such as electroporation of plant seed cells with DNA or by transformation of cells with expression vectors capable of expressing or over expressing the proteins of the invention or fragments thereof that are capable of inhibiting cell or viral growth.

Alternatively, the method uses an expression vector capable of producing anti-sense RNA of the cDNA of the invention.

Another one of the specific characteristics of the plants protein and of the nucleic acids includes a N-terminal domain corresponding in sequence to the amino acids 1 to 90 of the SEQ ID No. 2 and a nucleotides sequence corresponding to bases 31 to 300 of the SEQ ID No. 1. These sequences are characterized by possessing less than 150 and less than 450 units that the animal sequences which possess more than 300 amino acids and 900 pairs of more bases.

DETAILED DESCRIPTION OF THE INVENTION

The present invention will now be illustrated further by reference to the following non-limiting Examples. Further embodiments falling within the scope of the claims attached hereto will occur to those skilled in the light of these.

EXAMPLE 1

Figure 1:
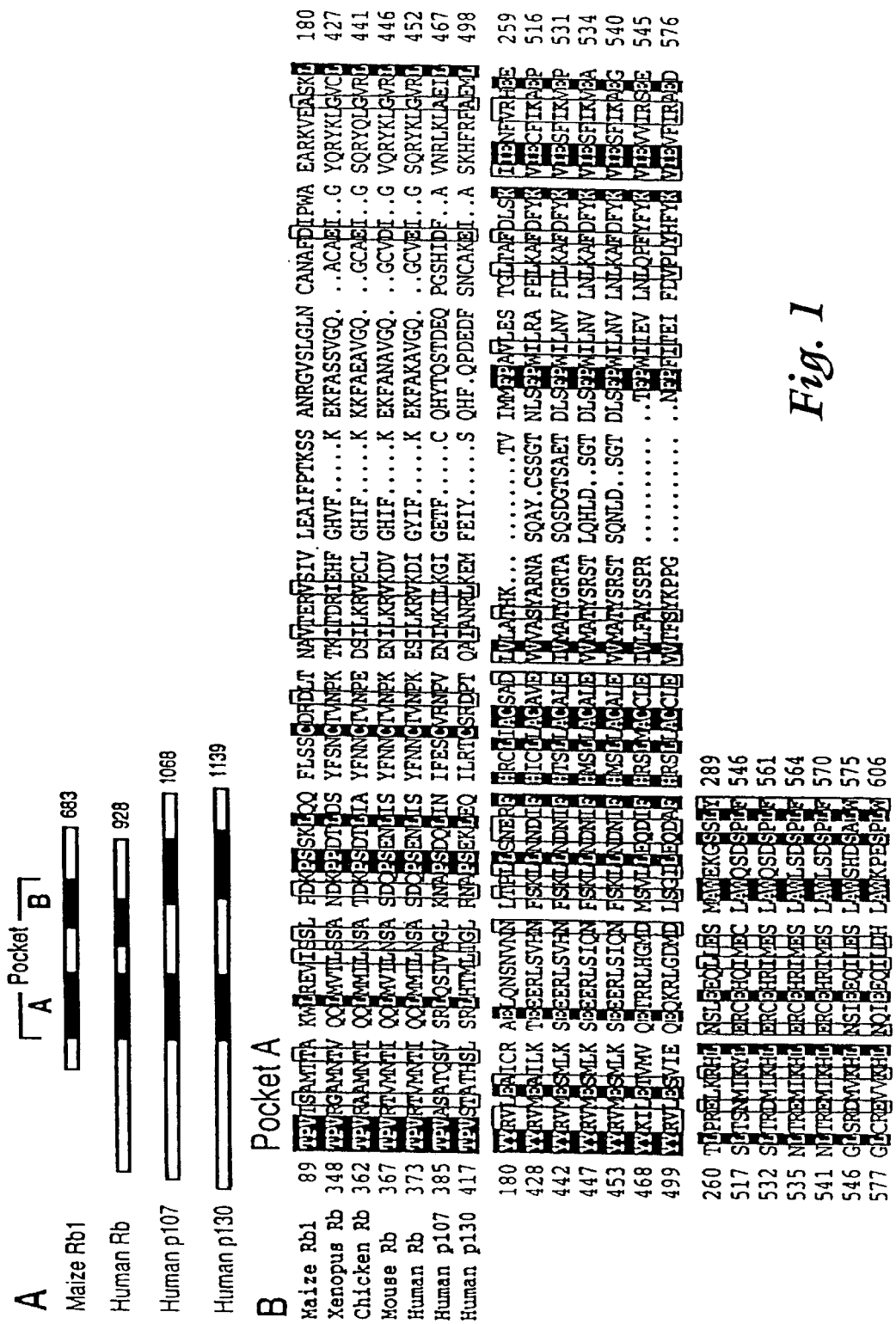
FIG. 1. The sub-figure A shows the relative lengths of the present ZmRb1 protein and the human retinoblastoma proteins. The sub-figure B shows the alignment of the amino acids sequences of the Pocket A and Pocket B of the ZmRb1 with that of the Xenopus, chicken, rat and three human protein (Rb, p107 and p130) (SEQ ID NOs:6–19).
Figure 2:
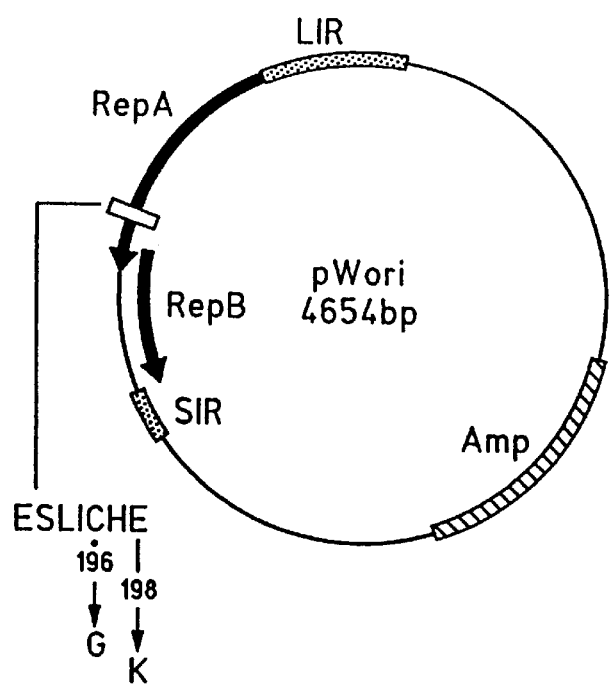
FIG. 2. This figure is a map of the main characteristics of the WDV virus and the pwori vector derived from WDV and the positions of the deletions and mutations used in order to establish that the LXCXE motif is required for its replication in plants cells.
Figure 2:
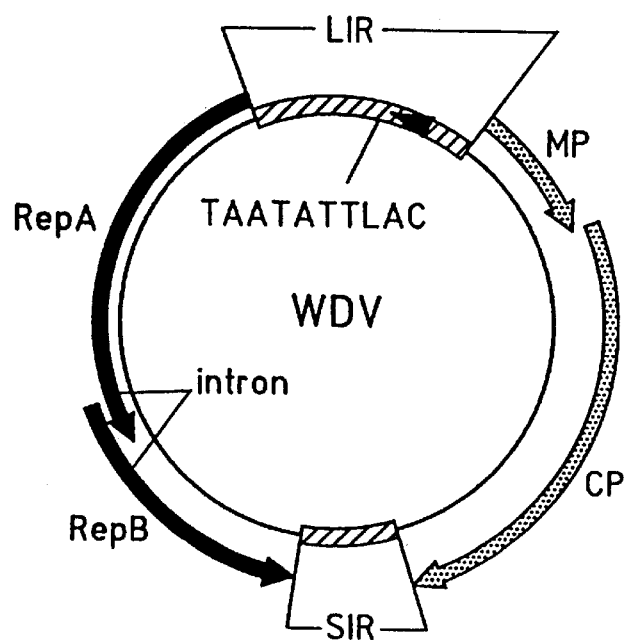

Isolation of DNA and Protein Expressing Clones.

Total RNA was isolated from maize root and mature leaves by grinding the material previously frozen in liquid nitrogen essentially as described in Soni et al (1995). The major and minor p75ZmRb1 mRNAs were is identified by hybridization to a random-primed 32P-labelled PstI internal fragment (1.4 kb).

A portion of a maize cDNA library (106 pfu) in 1ZAPII (Stratagene) was screened by subsequent hybridization to 5'-labelled oligonucleotides designed to be complementary to a known EST sequence of homologue maize of p130. These otigonucleotides were 5'-AATAGACACATCGATCAA/G (SEQ ID NO:3) (M.5m, nt positions 1411–1438) and 5'-GTAATGATACCAACATGG (SEQ ID NO:4) (M.3c, nt positions 1606–1590) (Isogen Biosciences).

After the second round of screening, pBluescript SK-(pBS) phagemids from positive clones were isolated by in vivo excision with ExAssist helper phage (Stratagene) according to protocols recommended by the manufacturer. DNA sequencing was carried out using a SequenaseTM Kit (USB).

The 5'-end of the mRNAs encoding p75ZmRb1 was determined by RACE-PCR. Poly-A+mRNA was purified by chromatography on oligo-dT-cellulose (Amersham). The first strand was synthesized using oligonucleotide Dral35 (5'-GATTTAAAATCAAGCTCC (SEQ ID NO:5), nt positions 113–96). After denaturation at 90° C. for 3 min, RNA was eliminated by RNase treatment, the cDNA recovered and 5'-tailed with terminal transferase and dATP. Then a PCR fragment was amplified using primer Dral35 and the linker-primer (50 bp) of the Stratagene cDNA synthesis kit.

One of the positive clones so produced contained a ~4 kb insert that, according to restriction analysis, extended both 5' and 3' of the region contained in the Expressed Sequence Tag used. The nucleotide sequence corresponding to the longest cDNA insert (3747 bp) is shown in SEQ ID No. 1. This ZmRb1 cDNA contains a single open reading frame capable of encoding a protein of 683 amino acids (predicted Mr 75247, p75ZmRb1) followed by a 1646 bp 3'-untranslated region. Untranslated regions of similar length have been also found in mammalian Rb cDNAs (Lee, W.-L. et al, Science 235, 1394 (1987); Bernards, R. et al, Proc. Natl. Acad. Sci. USA 86, 6474 (1989)). Northern analysis indicates that maize cells derived from both root meristems and mature leaves contain a major message, ~2.7±0.2 kb in length. In addition, a minor ~3.7±0.2 kb message also appears. Heterogeneous transcripts have been detected in other species (Destrée, O. H. J. et al, Dev. Biol. 153, 141 (1992)).

Plasmid pWoriΔΔ was constructed by deleting in pWori most of the sequences encoding WDV proteins (Sanz and Gutierrez, unpublished). Plasmid p35S.Rb1 was constructed by inserting the CaMV 35S promoter (obtained from pWDV3:35SGUS) upstream of the ZmRb1 cDNA in the pBS vector. Plasmid p35S.130 was constructed by introducing the complete coding sequence of human p130 instead of ZmRb1 sequences into p35S.Rb1. Plasmid p35. A+B was constructed by substituting sequences encoding the WDV RepA and RepB ORFs instead of ZmRb1 in p35S.Rb1 plasmid. (See Soni, R. and Murray, J. A. H. Anal. Biochem. 218, 474–476 (1994)).

The sequence around the methionine codon at nucleotide position 31 contains a consensus translation start (Kozak, M. J. Mol. Biol. 196, 947 (1987)). To determine whether the CDNA contained the full-length ZmRb1 coding region, the 5'-end of the mRNAs was amplified by RACE-PCR using an oligonucleotide derived from a region close to the putative initiator AUG, which would produce a fragment of ~150 bp. The results are consistent with the ZmRb1 CDNA clone containing the complete coding region.

The ZmRb1 protein contains segments homologous to the A and B subdomains of the "pocket" that is present in all members of the Rb family. These subdomains are separated by a non-conserved spacer. ZmRb1 also contains non-conserved N-terminal and C-terminal domains. Overall, ZmRb1 shares ~28–30% amino acid identity (~50% similarity) with the Rb family members (Hannon, G. J., Demetrick, D. & Beach, D. Genes Dev. 7, 2378 (1993); Cobrinik, D., Whyte, P., Peeper, D. S., Jacks, T. & Weinberg, R. A. ibid., p. 2392 (1993). Ewen, M. E., Xing, Y. Lawrence, J. B. and Livingston, D. M. Cell 66, 1155 (1991))(Lee W. L. et al, Science 235, 1394 (1987); Bernards et al, Proc. Natl. Acad. Sci. USA 86, 6974 (1989)), with the A and B subdomains exhibiting the highest homology (~50–64%). Interestingly, amino acid C706 in human Rb, critical for its function (Kaye, F. J., Kratzke R. A., Gerster, J. L. and Horowitz, J. M. Proc. Natl. Acad. Sci. USA 87, 6922 (1990)), is also conserved in maize p75ZmRb1.

Note: The 561–577 amino acids encompass a proline-rich domain.

ZmRb1 contains 16 consensus sites, SP or TP for phosphorylation by cyclins dependant kinases (CDKs) with one of the 5'-tail of the sub-domain A and several in the C-terminal area which are potential sites of phosphorylation. A nucleic acid preferred group which encodes proteins in which one or more of these sites are changed or deleted, making the protein more resistant to the phosphorylation and thus, to its functionality, for example linking to E2F or similar. This can be easily carried out by means of mutagenesis conducted by means of PCR.

EXAMPLE 2

In vivo Activity

Replication of wheat dwarf geminivirus (WDV) is dependent upon an intact LXCXE motif of the viral RepA protein. This motif can mediate interaction with a member of the human Rb family, p130, in yeasts. Therefore, the inventors investigated whether p75ZmRb1 could complex with WDV RepA by using the yeast two-hybrid system (Fields, S. and Song, O. Nature 340, 245–246 (1989)). Yeast cells were co-transformed with a plasmid encoding the fusion GAL4BD-RepA protein and with plasmids encoding different GAL4AD fusion protein. The GAL4AD-p75ZmRb1 fusion could also complex with GAL4BD-RepA to allow growth of the recipient yeast cells in the absence of histidine. This interaction was slightly stronger than that seen with the human p130 protein. RepA could also bind to some extent to a N-terminally truncated form of p75ZmRb1. The role of the LXCXE motif in RepA-p75ZmRb1 interaction was assessed using a point mutation in WDV RepA (E198K) which we previously showed to destroy interaction with human p130. Co-transformation of ZmRb1 with a plasmid encoding the fusion GAL4BD-RepA(E198K) indicated that the interaction between RepA and p75ZmRb1 occurred through the LXCXE motif.

In this respect, the E198K mutant of WDV RepA behaves similarly to analogous point mutants of animal virus oncoproteins (Moran, E., Zerler, B., Harrison, T. M. and Mathews, M. B. Mol. Cell Biol. 6, 3470 (1986); Cherington, V. et al., ibid., p. 1380 (1988); Lillie, J. W., Lowenstein, P. M., Green, M. R. and Green, M. Cell 50, 1091 (1987); DeCarpio, J. A. et al., ibid., p. 275 (1988)).

Specific interaction between maize p75ZmRb1 and WDV RepA in the yeast two-hybrid system (Fields et al) relied on the ability to reconstitute a functional GAL4 activity from two separated GAL4 fusion proteins containing the DNA binding domain (GAL4BD) and the activation domain (GAL4AD). Yeast HF7c cells were co-transformed with a plasmid expressing the GAL4BD-RepA or the GAL4BD-RepA(E198K) fusions and the plasmids expressing the GAL4AD alone (Vec) or fused to human p130, maize p75 (p75ZmRb1) or a 69 amino acids N-terminal deletion of p75 (p75ZmRb1-DN). Cells were streaked on plates with or without histidine according to the distribution shown in the upper left corner. The ability to grow in the absence of histidine depends on the functional reconstitution of a GAL4 activity upon interaction of the fusion proteins, since this triggers expression of the HIS3 gene which is under the control of a GAL4 responsive element. The growth characteristics of these yeast co-transformants correlate with the levels of b-galactosidase activity.

Procedures for two-hybrid analysis are described in Xie et al (1995). The GAL4AD-ZmRb1 fusions were construed in the pGAD424 vector.

EXAMPLE 3

In vivo Activity

Geminivirus DNA replication requires the cellular DNA replication machinery as well as other S-phase specific factors (Davies, J. W. and Stanley, J. Trends Genet. 5, 77 (1989); Lazarowitz, S. Crit. Rev. Plant Sci. 11, 327 (1992)). Consistent with this requirement, geminivirus infection appears to drive non-proliferating cells into S-phase, as indicated by the accumulation of the proliferating cell nuclear antigen (PCNA), a protein which is not normally present in the nuclei of differentiated cells (Nagar, S., Pedersen, T. J., Carrick, K. M., Hanley-Bowdoin, L. and Robertson, D. Plant Cell 7, 705 (1995)). The inventors finding that efficient WDV DNA replication requires an intact LXCXE motif in RepA coupled with the discovery of a plant homolog of Rb supports the model that, as in animal cells, sequestration of plant Rb by viral RepA protein promotes inappropriate entry of infected cells into S-phase. Therefore, one way to investigate the function of p75ZmRb1 was to measure geminivirus DNA replication in cells transfected with a plasmid bearing the ZmRb1 sequences under a promoter functional in plant cells, an approach analogous to that previously used in human cells (Uzvolgi, E. et al., Cell Growth Diff 2, 297 (1991)). Accumulation of newly replicated viral plasmid DNA was impaired in wheat cells transfected with plasmids expressing p75ZmRb1 or human p130, when expression of WDV replication protein(s) is directed either by the WDV promoter or by the CaMV 35S promoter.

Since WDV DNA replication requires an S-phase cellular environment, interference with viral DNA replication by p75ZmRb1 and human p130 strongly evidences a role for retinoblastoma protein in the control of the G1/S transition in plants. The existence of a plant Rb homolog implies that despite their ancient divergence, plant and animal cells use, at least in part, similar regulatory proteins and pathways for cell cycle control.

Two lines of evidences reinforce this model. First, a gene encoding a protein that complements specifically the G1/S, but not the G2/M transition of the budding yeast cdc28 mutant has been identified in alfalfa cells (Hirt, H., Páy, A., Bögre, L., Meskiene, I. and Heberle-Bors, E. Plant J. 4, 61 (1993)). Second, plant homologs of D-type cyclins have been isolated from Arabidopsis and these, like their mammalian relatives, contain LXCXE motifs. In concert with plant versions of CDK4 and CDK6, plant D-type cyclins may regulate passage through G1 phase by controlling the phosphorylation state of Rb-like proteins.

In animal cells, the Rb family has been implicated in tumor suppression and in the control of differentiation and development. Thus, p75ZmRb1 could also play key regulatory roles at other levels during the plant cell life. One key question that is raised by the existence of Rb homologs in plant cells is whether, as in animals disruption of the Rb pathway leads to a tumor-prone condition. In this regard, the inventors have noted that the VirB4 protein encoded by the Ti plasmids of both *Agrobacterium tumefaciens* and *A. rhyzogenes* contains an LXCXE motif. Although the VirB4 protein is required for tumor induction (Hooykas, P. J. J. and Beijersbergen, A. G. M. Annu. Rev. Phytopathol. 32, 157 (1994), the function of its LXCXE motif in this context remains to be examined. Geminivirus infection is not accompanied by tumor development in the infected plant, but in some cases an abnormal growth of enactions has been observed (G. Dafalla and B. Gronenborn, personal communication).

Inhibition of wheat dwarf geminivirus (WDV) DNA replication by ZmRb1 or human p130 in cultured wheat cells was carried out as follows. A. Wheat cells were transfected, as indicated, with pwori (Xie et al. 1995) alone (0.5 µg), a replicating WDV-based plasmid which encodes WDV proteins required for viral DNA replication, and with control plasmid pBS (10 µg) or p35S.Rb1 (10 µg), which encodes ZmRb1 sequences under the control of the CaMV 35S promoter. Total DNA was purified one and two days after transfection, equal amounts fractionated in agarose gels and ethidium bromide staining and viral pwori DNA identified by Southern hybridization. Plasmid DNA represents exclusively newly-replicated plasmid DNA since it is fully resistant to DpnI digestion and sensitive to MboI. Note that the MboI-digested samples were run for about half of the length than the undigested samples. B. To test the effect of human p130 on WDV DNA replication, wheat cells were co-transfected with pwori (0.5 µg) and plasmids pBS (control), p35S.Rb1 or p35S.130 (10 µg in each case). Replication of the test plasmid (pWori) was analyzed two days after transfection and was detected as described in part A using ethidium bromide staining; and Southern hybridization. C. To test the effect of ZmRb1 or human p130 on WDV DNA replication when expression of viral proteins was directed by the CaMV 35S promoter, the test plasmid pWoriΔΔ (which does not encode functional WDV replication proteins but replicates when they are provided by a different plasmid, i. e. pWori) was used. Wheat cells were co-transfected, as indicated, with pWoriΔΔ (0.25 µg), pWori (0.25 µg), p35S.A+B (6 µg), p35S.Rb1 (10 µg) and/or p35S.130 (10 µg). Replication of the test plasmid (pWoriΔΔ) was analyzed 36 hours after transfection and was detected as described in part A using ethidium bromide staining; Southern hybridization. Plasmids pWori (M1) and pWoriΔΔ (M2; Sanz and Gutierrez, unpublished), 100 pg in each case, were used as markers. Suspension cultures of wheat cells, transfection by particle bombardment and analysis of viral DNA replication were carried out as described in (Xie et al. 1995), except that DNA extraction was modified as in (Soni and Murray. Arnal. Biochem. 218, 474–476 (1995).

What is claimed is:

1. A recombinant nucleic acid comprising a promoter sequence that is functional in plants operably linked to a polynucleotide sequence encoding a retinoblastoma protein that inhibits the function of E2F transcription factors in a plant cell wherein said polynucleotide sequence is selected from the group consisting of bases 31–207 of SEQ ID NO: 2, sequences encoding the amino acid sequence of SEQ ID NO: 1, and sequences that hybridize with the polynucleotide of SEQ ID NO: 2 under conditions comprising 65° C. and 0.2×SSPE, wherein said protein has the plant virus replication inhibitory activity, viral Rep protein binding properties and activity of inhibiting the function of plant E2F transcription factors of SEQ ID NO: 2.

2. A method of producing a retinoblastoma protein that interacts with a viral LXCXE motif in a plant cell comprising expressing the recombinant nucleic acid as claimed in claim 1.

3. A recombinant vector comprising a recombinant nucleic acid as claimed in claim 1.

4. A plant cell comprising a recombinant nucleic acid as claimed in claim 1.

5. A transgenic plant comprising a cell as claimed in claim 4.

6. A recombinant nucleic acid as claimed in claim 1, wherein the promoter is selected from the group consisting of the CaMV 35S promoter and the Wheat Dwarf Virus promoter.

* * * * *

SEQUENCE LISTING

<160> NUMBER OF SEQ ID NOS: 19

<210> SEQ ID NO 1
<211> LENGTH: 683
<212> TYPE: PRT
<213> ORGANISM: Unknown Organism
<220> FEATURE:
<223> OTHER INFORMATION: Description of Unknown Organism: plant RB protein

<400> SEQUENCE: 1

```
Met Glu Cys Phe Gln Ser Asn Leu Glu Lys Met Glu Lys Leu Cys Asn
  1               5                  10                  15

Ser Asn Ser Cys Lys Gly Glu Leu Asp Phe Lys Ser Ile Leu Ile Asn
             20                  25                  30

Asn Asp Tyr Ile Pro Tyr Asp Glu Asn Ser Thr Gly Asp Ser Thr Asn
         35                  40                  45

Leu Gly His Ser Lys Cys Ala Phe Glu Thr Leu Ala Ser Pro Thr Lys
     50                  55                  60

Thr Ile Lys Asn Met Leu Thr Val Pro Ser Ser Pro Leu Ser Pro Ala
 65                  70                  75                  80

Thr Gly Gly Ser Val Lys Ile Val Gln Met Thr Pro Val Thr Ser Ala
                 85                  90                  95

Met Thr Thr Ala Lys Trp Leu Arg Glu Val Ile Ser Ser Leu Pro Asp
            100                 105                 110

Lys Pro Ser Ser Lys Leu Gln Gln Phe Leu Ser Ser Cys Asp Arg Asp
        115                 120                 125

Leu Thr Asn Ala Val Thr Glu Arg Val Ser Ile Val Leu Glu Ala Ile
    130                 135                 140

Phe Pro Thr Lys Ser Ser Ala Asn Arg Gly Val Ser Leu Gly Leu Asn
```

-continued

```
            145                 150                 155                 160
        Cys Ala Asn Ala Phe Asp Ile Pro Trp Ala Glu Ala Arg Lys Val Glu
                        165                 170                 175
        Ala Ser Lys Leu Tyr Tyr Arg Val Leu Glu Ala Ile Cys Arg Ala Glu
                        180                 185                 190
        Leu Gln Asn Ser Asn Val Asn Asn Leu Thr Pro Leu Leu Ser Asn Glu
                        195                 200                 205
        Arg Phe His Arg Cys Leu Ile Ala Cys Ser Ala Asp Leu Val Leu Ala
                        210                 215                 220
        Thr His Lys Thr Val Ile Met Met Phe Pro Ala Val Leu Glu Ser Thr
        225                 230                 235                 240
        Gly Leu Thr Ala Phe Asp Leu Ser Lys Ile Ile Glu Asn Phe Val Arg
                        245                 250                 255
        His Glu Glu Thr Leu Pro Arg Glu Leu Lys Arg His Leu Asn Ser Leu
                        260                 265                 270
        Glu Glu Gln Leu Leu Glu Ser Met Ala Trp Glu Lys Gly Ser Ser Leu
                        275                 280                 285
        Tyr Asn Ser Leu Ile Val Ala Arg Pro Ser Val Ala Ser Glu Ile Asn
                        290                 295                 300
        Arg Leu Gly Leu Leu Ala Glu Pro Met Pro Ser Leu Asp Asp Leu Val
        305                 310                 315                 320
        Ser Arg Gln Asn Val Arg Ile Glu Gly Leu Pro Ala Thr Pro Ser Lys
                        325                 330                 335
        Lys Arg Ala Ala Gly Pro Asp Asp Asn Ala Asp Pro Arg Ser Pro Lys
                        340                 345                 350
        Arg Ser Cys Asn Glu Ser Arg Asn Thr Val Val Glu Arg Asn Leu Gln
                        355                 360                 365
        Thr Pro Pro Pro Lys Gln Ser His Met Val Ser Thr Ser Leu Lys Ala
        370                 375                 380
        Lys Cys His Pro Leu Gln Ser Thr Phe Ala Ser Pro Thr Val Cys Asn
        385                 390                 395                 400
        Pro Val Gly Gly Asn Glu Lys Cys Ala Asp Val Thr Ile His Ile Phe
                        405                 410                 415
        Phe Ser Lys Ile Leu Lys Leu Ala Ala Ile Arg Ile Arg Asn Leu Cys
                        420                 425                 430
        Glu Arg Val Gln Cys Val Glu Gln Thr Glu Arg Val Tyr Asn Val Phe
                        435                 440                 445
        Lys Gln Ile Leu Glu Gln Gln Thr Thr Leu Phe Phe Asn Arg His Ile
                        450                 455                 460
        Asp Gln Leu Ile Leu Cys Cys Leu Tyr Gly Val Ala Lys Val Cys Gln
        465                 470                 475                 480
        Leu Glu Leu Thr Phe Arg Glu Ile Leu Asn Asn Tyr Lys Arg Glu Ala
                        485                 490                 495
        Gln Cys Lys Pro Glu Val Phe Ser Ser Ile Tyr Ile Gly Ser Thr Asn
                        500                 505                 510
        Arg Asn Gly Val Leu Val Ser Arg His Val Gly Ile Ile Thr Phe Tyr
                        515                 520                 525
        Asn Glu Val Phe Val Pro Ala Ala Lys Pro Phe Leu Val Ser Leu Ile
                        530                 535                 540
        Ser Ser Gly Thr His Pro Glu Asp Lys Lys Asn Ala Ser Gly Gln Ile
        545                 550                 555                 560
        Pro Gly Ser Pro Lys Pro Ser Pro Phe Pro Asn Leu Pro Asp Met Ser
                        565                 570                 575
```

```
Pro Lys Lys Val Ser Ala Ser His Asn Val Tyr Val Ser Pro Leu Arg
            580                 585                 590

Gln Thr Lys Leu Asp Leu Leu Leu Ser Pro Ser Ser Arg Ser Phe Tyr
        595                 600                 605

Ala Cys Ile Gly Glu Gly Thr His Ala Tyr Gln Ser Pro Ser Lys Asp
    610                 615                 620

Leu Ala Ala Ile Asn Ser Arg Leu Asn Tyr Asn Gly Arg Lys Val Asn
625                 630                 635                 640

Ser Arg Leu Asn Phe Asp Met Val Ser Asp Ser Val Val Ala Gly Ser
                645                 650                 655

Leu Gly Gln Ile Asn Gly Gly Ser Thr Ser Asp Pro Ala Ala Ala Phe
            660                 665                 670

Ser Pro Leu Ser Lys Lys Arg Glu Thr Asp Thr
            675                 680
```

<210> SEQ ID NO 2
<211> LENGTH: 3747
<212> TYPE: DNA
<213> ORGANISM: Zea mays

<400> SEQUENCE: 2

```
gaattcggca cgagcaaagg tctgattgat atggaatgtt tccagtcaaa tttggaaaaa      60
atggagaaac tatgtaattc taatagctgt aaagggagc ttgattttaa atcaattttg     120
atcaataatg attatattcc ctatgatgag aactcgacgg gggattccac caatttagga    180
cattcaaagt gtgcctttga aacattggca tctcccacaa agacaataaa gaacatgctg    240
actgttccta gttctccttt gtcaccagcc accggtggtt cagtcaagat tgtgcaaatg    300
acaccagtaa cttctgccat gacgacagct aagtggcttc gtgaggtgat atcttcattg    360
ccagataagc cttcatctaa gcttcagcag tttctgtcat catgcgatag ggatttgaca    420
aatgctgtca cagaaagggt cagcatagtt ttggaagcaa ttttttccaac caaatcttct    480
gccaatcggg gtgtatcgtt aggtctcaat tgtgcaaatg cctttgacat tccgtgggca    540
gaagccagaa aagtggaggc ttccaagttg tactataggg tattagaggc aatctgcaga    600
gcggagttac aaaacagcaa tgtaaataat ctaactccat tgctgtcaaa tgagcgtttc    660
caccgatgtt tgattgcatg ttcagcggac ttagtattgg cgacacataa gacagtcatc    720
atgatgtttc ctgctgttct tgagagtacc ggtctaactg catttgattt gagcaaaata    780
attgagaact tgtgagaca tgaagagacc ctcccaagag aattgaaaag gcacctaaat     840
tccttagaag aacagctttt ggaaagcatg gcatgggaga aaggttcatc attgtataac    900
tcactgattg ttgccaggcc atctgttgct tcagaaataa accgccttgg tcttttggct    960
gaaccaatgc catctcttga tgacttagtg tcaaggcaga atgttcgtat cgagggcttg   1020
cctgctacac catctaaaaa acgtgctgct ggtccagatg acaacgctga tcctcgatca   1080
ccaaagagat cgtgcaatga atctaggaac acagtagtag agcgcaattt gcagacacct   1140
ccacccaagc aaagccacat ggtgtcaact agtttgaaag caaaatgcca tccactccag   1200
tccacatttg caagtccaac tgtctgtaat cctgttggtg ggaatgaaaa atgtgctgac   1260
gtgacaattc atatattctt ttccaagatt ctgaagttgg ctgctattag aataagaaac   1320
ttgtgcgaaa gggttcaatg tgtggaacag acagagcgtg tctataatgt cttcaagcag   1380
attcttgagc aacagacaac attattttt aatagacaca tcgatcaact tatcctttgc   1440
tgtctttatg gtgttgcaaa ggtttgtcaa ttagaactca cattcaggga gatactcaac   1500
```

-continued

```
aattacaaaa gagaagcaca atgcaagcca gaagttttt  caagtatcta tattgggagt   1560
acgaaccgta atgggtatt  agtatcgcgc catgttggta tcattacttt ttacaatgag   1620
gtatttgttc cagcagcgaa gcctttcctg gtgtcactaa tatcatctgg tactcatcca   1680
gaagacaaga agaatgctag tggccaaatt cctggatcac ccaagccatc tcctttccca   1740
aatttaccag atatgtcccc gaagaaagtt tcagcatctc ataatgtata tgtgtctcct   1800
ttgcggcaaa ccaagttgga tctactgctg tcaccaagtt ccaggagttt ttatgcatgc   1860
attggtgaag gcacccatgc ttatcagagc ccatctaagg atttggctgc tataaatagc   1920
cgcctaaatt ataatggcag gaaagtaaac agtcgattaa atttcgacat ggtgagtgac   1980
tcagtggtag ccggcagtct gggccagata atggtggtt  ctacctcgga tcctgcagct   2040
gcatttagcc ccctttcaaa gagagagag  acagatactt gatcaattat aaatggtggc   2100
ctctctcgta tatagctcac agatccgtgc tccgtagcag tctattcttc tgaataagtg   2160
gattaactgg agcgatttaa ctgtacatgt atgtgttagt gagaagcagc agttttagg    2220 cagcaaactg tttcaagtta gcttttgagc tatcaccatt tctctgctga ttgaacatat   2280
ccgctgtgta gagtgctaat gaatctttag ttttcattgg gctgacataa caaatcttta   2340
tcctagttgg ctggttgttg ggaggcattc atcagggtta tatttggttg tcaaaaagta   2400
ctgtacttaa ttcacatctt tcacattttt cactagcaat agcagcccca aattgctttc   2460
ctgactagga acatattctt tacaggtata agcatgccaa ctctaaacta tatgaatcct   2520 tttatattc  tcatttttaa gtacttctct gtttctgcta cttttgtact gtatatttcc   2580
agcttctcca tcagactgat gatcccatat tcagtgtgct gcaagtgatt tgaccatatg   2640
tggcttatcc ttcaggtatg tctcatgttg tgacttcatt gctgattgct tttgtaatgg   2700
tactgttgag ttcatttctg gttacaatca gcctttactg cttatattg  ttctactaat   2760 tttggcttgc acagccagga cgattggttt tctgcatcaa tcaatctttt ttaggacaag   2820 atattttgt  atgctacact tcccaaattg caattaatcc agaagtctac cttgttttat   2880
tctattagtt ctcagcaaca gtgaatgaat atgaatcagt catgctgata gatgttcatc   2940
tggttattcc aaacaatctg acatcgcatc tctttctgca agtgagatga agaaaacctg   3000
aaatgctatc accatttaaa acattggctt ctggaagttc aggtgattag caggagacgt   3060
tctgacattg ccattgacat gtacggtagt gatggcagga gacgttctta aacagcagct   3120
gctccttcag cttgtaatgt ctgattgtat tgaccaagag catccacctt gccttatggt   3180
actaactgaa tgagctggtg acgctgactc atctgcataa tggcagatgc ttaaccatct   3240
ttaggagctc atgtcatgat tccagctgca ccgtgtcaaa tgtgaaggcc ctgcaaggct   3300
ttccaggccg caccaatcct gcttgcttct tgaagataca tatggtgcca cctaaataaa   3360
agctgtttct ggttatgtct gtccttgaca tgtcaacaga ttagtgttgg gttgcagtca   3420
tgtggtgttt aagtcttgga gaaggcgaga agtcattgct gccagcattg tgatcgtcag   3480
gcacagaagt actcaaaagt gagagctact tgttgcgagc aaacggaggg cgatataggt   3540
tgatagccaa tttcagttct ctatatacaa gcagcggatt ttgtttagag ttagcttttg   3600
agatgcatca tttcttcac  atctgattct gtgtgttgta actcggagtc gcgtagaagt   3660
tagaatgcta actgacctta attttcaccg aataatttgc tagcgttttt cagtatgaaa   3720
tccttgtctt aaaaaaaaaa aaaaaaa                                       3747
```

<210> SEQ ID NO 3

```
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 3
aatagacaca tcgatcaag                                                    19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 4
gtaatgatac caacatgg                                                     18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
gatttaaaat caagctcc                                                     18

<210> SEQ ID NO 6
<211> LENGTH: 199
<212> TYPE: PRT
<213> ORGANISM: Zea mays

<400> SEQUENCE: 6

Thr Pro Val Thr Ser Ala Met Thr Thr Ala Lys Trp Leu Arg Glu Val
  1               5                  10                  15

Ile Ser Ser Leu Pro Asp Lys Pro Ser Ser Lys Leu Gln Gln Phe Leu
             20                  25                  30

Ser Ser Cys Asp Arg Asp Leu Thr Asn Ala Val Thr Glu Arg Val Ser
         35                  40                  45

Ile Val Leu Glu Ala Ile Phe Pro Thr Lys Ser Ser Ala Asn Arg Gly
     50                  55                  60

Val Ser Leu Gly Leu Asn Cys Ala Asn Ala Phe Asp Ile Pro Trp Ala
 65                  70                  75                  80

Glu Ala Arg Lys Val Glu Ala Ser Lys Leu Tyr Tyr Arg Val Leu Glu
                 85                  90                  95

Ala Ile Cys Arg Ala Glu Leu Gln Asn Ser Asn Val Asn Asn Leu Thr
            100                 105                 110

Pro Leu Leu Ser Asn Glu Arg Phe His Arg Cys Leu Ile Ala Cys Ser
        115                 120                 125

Ala Asp Leu Val Leu Ala Thr His Lys Thr Val Ile Met Met Phe Pro
    130                 135                 140

Ala Val Leu Glu Ser Thr Gly Leu Thr Ala Phe Asp Leu Ser Lys Ile
145                 150                 155                 160

Ile Glu Asn Phe Val Arg His Glu Glu Thr Leu Pro Arg Glu Leu Lys
                165                 170                 175

Arg His Leu Asn Ser Leu Glu Glu Gln Leu Leu Glu Ser Met Ala Trp
            180                 185                 190

Glu Lys Gly Ser Ser Leu Tyr
```

<210> SEQ ID NO 7
<211> LENGTH: 199
<212> TYPE: PRT
<213> ORGANISM: Xenopus sp.

<400> SEQUENCE: 7

Thr Pro Val Arg Gly Ala Met Asn Thr Val Gln Gln Leu Met Val Thr
 1               5                  10                  15

Leu Ser Ser Ala Asn Asp Lys Pro Pro Asp Thr Leu Asp Ser Tyr Phe
             20                  25                  30

Ser Asn Cys Thr Val Asn Pro Lys Thr Lys Ile Thr Asp Arg Ile Glu
         35                  40                  45

His Phe Gly His Val Phe Lys Glu Lys Phe Ala Ser Ser Val Gly Gln
     50                  55                  60

Ala Cys Ala Glu Ile Gly Tyr Gln Arg Tyr Lys Leu Gly Val Cys Leu
 65                  70                  75                  80

Tyr Tyr Arg Val Met Glu Ala Ile Leu Lys Thr Glu Glu Arg Leu
                 85                  90                  95

Ser Val His Asn Phe Ser Lys Leu Leu Asn Asn Asp Ile Phe His Ile
                100                 105                 110

Cys Leu Leu Ala Cys Ala Val Glu Val Val Ala Ser Tyr Ala Arg
             115                 120                 125

Asn Ala Ser Gln Ala Tyr Cys Ser Ser Gly Thr Asn Leu Ser Phe Pro
         130                 135                 140

Trp Ile Leu Arg Ala Phe Glu Leu Lys Ala Phe Asp Phe Tyr Lys Val
145                 150                 155                 160

Ile Glu Cys Phe Ile Lys Ala Glu Pro Ser Leu Thr Ser Asn Met Ile
                165                 170                 175

Lys Tyr Leu Glu Arg Cys Glu His Gln Ile Met Glu Cys Leu Ala Trp
                180                 185                 190

Gln Ser Asp Ser Pro Leu Phe
            195

<210> SEQ ID NO 8
<211> LENGTH: 200
<212> TYPE: PRT
<213> ORGANISM: Gallus sp.

<400> SEQUENCE: 8

Thr Pro Val Arg Ala Ala Met Asn Thr Ile Gln Gln Leu Met Met Ile
 1               5                  10                  15

Leu Asn Ser Ala Thr Asp Lys Pro Ser Asp Thr Leu Ile Ala Tyr Phe
             20                  25                  30

Asn Asn Cys Thr Val Asn Pro Glu Asp Ser Ile Leu Lys Arg Val Glu
         35                  40                  45

Cys Leu Gly His Ile Phe Lys Lys Phe Ala Glu Ala Val Gly Gln
     50                  55                  60

Gly Cys Ala Glu Ile Gly Ser Gln Arg Tyr Gln Leu Gly Val Arg Leu
 65                  70                  75                  80

Tyr Tyr Arg Val Met Glu Ser Met Leu Lys Ser Glu Glu Glu Arg Leu
                 85                  90                  95

Ser Val His Asn Phe Ser Lys Leu Leu Asn Asp Asn Ile Phe His Thr
                100                 105                 110

Ser Leu Leu Ala Cys Ala Leu Glu Ile Val Met Ala Thr Tyr Gly Arg

```
                115                 120                      125
    Thr Ala Ser Gln Ser Asp Gly Thr Ser Ala Glu Thr Asp Leu Ser Phe
        130                 135                 140

Pro Trp Ile Leu Asn Val Phe Asp Leu Lys Ala Phe Asp Phe Tyr Lys
    145                 150                 155                 160

Val Ile Glu Ser Phe Ile Lys Val Glu Pro Ser Leu Thr Arg Asp Met
                        165                 170                 175

Ile Lys His Leu Glu Arg Cys Glu His Arg Ile Met Glu Ser Leu Ala
                    180                 185                 190

Trp Gln Ser Asp Ser Pro Leu Phe
                195                 200

<210> SEQ ID NO 9
<211> LENGTH: 198
<212> TYPE: PRT
<213> ORGANISM: Mus sp.

<400> SEQUENCE: 9

Thr Pro Val Arg Thr Val Met Asn Thr Ile Gln Gln Leu Met Val Ile
    1               5                   10                  15

Leu Asn Ser Ala Ser Asp Gln Pro Ser Glu Asn Leu Ile Ser Tyr Phe
                    20                  25                  30

Asn Asn Cys Thr Val Asn Pro Lys Glu Asn Ile Leu Lys Arg Val Lys
                35                  40                  45

Asp Val Gly His Ile Phe Lys Glu Lys Phe Ala Asn Ala Val Gly Gln
            50                  55                  60

Gly Cys Val Asp Ile Gly Val Gln Arg Tyr Lys Leu Gly Val Arg Leu
    65                  70                  75                  80

Tyr Tyr Arg Val Met Glu Ser Met Leu Lys Ser Glu Glu Arg Leu
                    85                  90                  95

Ser Ile Gln Asn Phe Ser Lys Leu Leu Asn Asp Asn Ile Phe His Met
                    100                 105                 110

Ser Leu Leu Ala Cys Ala Leu Glu Val Val Met Ala Thr Tyr Ser Arg
                115                 120                 125

Ser Thr Leu Gln His Leu Asp Ser Gly Thr Asp Leu Ser Phe Pro Trp
        130                 135                 140

Ile Leu Asn Val Leu Asn Leu Lys Ala Phe Asp Phe Tyr Lys Val Ile
    145                 150                 155                 160

Glu Ser Phe Ile Lys Val Glu Ala Asn Leu Thr Arg Glu Met Ile Lys
                        165                 170                 175

His Leu Glu Arg Cys Glu His Arg Ile Met Glu Ser Leu Ala Trp Leu
                    180                 185                 190

Ser Asp Ser Pro Leu Phe
                195

<210> SEQ ID NO 10
<211> LENGTH: 198
<212> TYPE: PRT
<213> ORGANISM: Homo sapiens

<400> SEQUENCE: 10

Thr Pro Val Arg Thr Val Met Asn Thr Ile Gln Gln Leu Met Met Ile
    1               5                   10                  15

Leu Asn Ser Ala Ser Asp Gln Pro Ser Glu Asn Leu Ile Ser Tyr Phe
                    20                  25                  30

Asn Asn Cys Thr Val Asn Pro Lys Glu Ser Ile Leu Lys Arg Val Lys
```

-continued

```
                35                  40                  45
Asp Ile Gly Tyr Ile Phe Lys Glu Lys Phe Ala Lys Ala Val Gly Gln
         50                  55                  60

Gly Cys Val Glu Ile Gly Ser Gln Arg Tyr Lys Leu Gly Val Arg Leu
 65                  70                  75                  80

Tyr Tyr Arg Val Met Glu Ser Met Leu Lys Ser Glu Glu Arg Leu
                 85                  90                  95

Ser Ile Gln Asn Phe Ser Lys Leu Leu Asn Asp Asn Ile Phe His Met
                100                 105                 110

Ser Leu Leu Ala Cys Ala Leu Glu Val Val Met Ala Thr Tyr Ser Arg
            115                 120                 125

Ser Thr Ser Gln Asn Leu Asp Ser Gly Thr Asp Leu Ser Phe Pro Trp
        130                 135                 140

Ile Leu Asn Val Leu Asn Leu Lys Ala Phe Asp Phe Tyr Lys Val Ile
145                 150                 155                 160

Glu Ser Phe Ile Lys Ala Glu Gly Asn Leu Thr Arg Glu Met Ile Lys
                165                 170                 175

His Leu Glu Arg Cys Glu His Arg Ile Met Glu Ser Leu Ala Trp Leu
            180                 185                 190

Ser Asp Ser Pro Leu Phe
            195
```

<210> SEQ ID NO 11
<211> LENGTH: 191
<212> TYPE: PRT
<213> ORGANISM: Homo sapiens

<400> SEQUENCE: 11

```
Thr Pro Val Ala Ser Ala Thr Gln Ser Val Ser Arg Leu Gln Ser Ile
  1               5                  10                  15

Val Ala Gly Leu Lys Asn Ala Pro Ser Asp Gln Leu Ile Asn Ile Phe
             20                  25                  30

Glu Ser Cys Val Arg Asn Pro Val Glu Asn Ile Met Lys Ile Leu Lys
         35                  40                  45

Gly Ile Gly Glu Thr Phe Cys Gln His Tyr Thr Gln Ser Thr Asp Glu
 50                  55                  60

Gln Pro Gly Ser His Ile Asp Phe Ala Val Asn Arg Leu Lys Leu Ala
 65                  70                  75                  80

Glu Ile Leu Tyr Tyr Lys Ile Leu Glu Thr Val Met Val Gln Glu Thr
                 85                  90                  95

Arg Arg Leu His Gly Met Asp Met Ser Val Leu Leu Glu Gln Asp Ile
            100                 105                 110

Phe His Arg Ser Leu Met Ala Cys Cys Leu Glu Ile Val Leu Phe Ala
        115                 120                 125

Tyr Ser Ser Pro Arg Thr Phe Pro Trp Ile Ile Glu Val Leu Asn Leu
130                 135                 140

Gln Pro Phe Tyr Phe Tyr Lys Val Ile Glu Val Val Ile Arg Ser Glu
145                 150                 155                 160

Glu Gly Leu Ser Arg Asp Met Val Lys His Leu Asn Ser Ile Glu Glu
                165                 170                 175

Gln Ile Leu Glu Ser Leu Ala Trp Ser His Asp Ser Ala Leu Trp
            180                 185                 190
```

<210> SEQ ID NO 12
<211> LENGTH: 200

```
<212> TYPE: PRT
<213> ORGANISM: Homo sapiens

<400> SEQUENCE: 12

Thr Pro Val Ser Thr Ala Thr His Ser Leu Ser Arg Leu His Thr Met
 1               5                  10                  15

Leu Thr Gly Leu Arg Asn Ala Pro Ser Glu Lys Leu Glu Gln Ile Leu
             20                  25                  30

Arg Thr Cys Ser Arg Asp Pro Thr Gln Ala Ile Ala Asn Arg Leu Lys
         35                  40                  45

Glu Met Gln Ala Ile Ala Asn Arg Leu Lys Glu Met Phe Glu Ile Tyr
     50                  55                  60

Ser Gln His Phe Gln Pro Asp Glu Asp Phe Ser Asn Cys Ala Lys Glu
 65                  70                  75                  80

Ile Ala Ser Lys His Phe Arg Phe Ala Glu Met Leu Tyr Tyr Arg Val
                 85                  90                  95

Leu Glu Ser Val Ile Glu Gln Glu Gln Lys Arg Leu Gly Asp Met Asp
            100                 105                 110

Leu Ser Gly Ile Leu Glu Gln Asp Ala Phe His Arg Ser Leu Leu Ala
        115                 120                 125

Cys Cys Leu Glu Val Val Thr Phe Ser Tyr Lys Pro Pro Gly Asn Phe
    130                 135                 140

Pro Phe Ile Thr Glu Ile Phe Asp Val Pro Leu Tyr His Phe Tyr Lys
145                 150                 155                 160

Val Ile Glu Val Phe Ile Arg Ala Glu Asp Gly Leu Cys Arg Glu Val
                165                 170                 175

Val Lys His Leu Asn Gln Ile Glu Glu Gln Ile Leu Asp His Leu Ala
            180                 185                 190

Trp Lys Pro Glu Ser Pro Leu Trp
        195                 200

<210> SEQ ID NO 13
<211> LENGTH: 137
<212> TYPE: PRT
<213> ORGANISM: Zea mays

<400> SEQUENCE: 13

Asn Glu Lys Cys Ala Asp Val Thr Ile His Ile Phe Phe Ser Lys Ile
 1               5                  10                  15

Leu Lys Leu Ala Ala Ile Arg Ile Arg Asn Leu Cys Glu Arg Val Gln
             20                  25                  30

Cys Val Glu Gln Thr Glu Arg Val Tyr Asn Val Phe Lys Gln Ile Leu
         35                  40                  45

Glu Gln Gln Thr Thr Leu Phe Phe Asn Arg His Ile Asp Gln Leu Ile
     50                  55                  60

Leu Cys Cys Leu Tyr Gly Val Ala Lys Val Cys Gln Leu Glu Leu Thr
 65                  70                  75                  80

Phe Arg Glu Ile Leu Asn Asn Tyr Lys Arg Glu Ala Gln Cys Lys Pro
                 85                  90                  95

Glu Val Phe Ser Ser Ile Tyr Ile Gly Ser Thr Asn Arg Asn Gly Val
            100                 105                 110

Leu Val Ser Arg His Val Gly Ile Ile Thr Phe Tyr Asn Glu Val Phe
        115                 120                 125

Val Pro Ala Ala Lys Pro Phe Leu Val
    130                 135
```

<210> SEQ ID NO 14
<211> LENGTH: 129
<212> TYPE: PRT
<213> ORGANISM: Xenopus sp.

<400> SEQUENCE: 14

Gln Gln Lys Ser Thr Ser Leu Ser Leu Phe Tyr Lys Lys Val Tyr Leu
 1               5                  10                  15

Leu Ala Tyr Lys Arg Leu Ser Ser Leu Cys Ser Ser Leu Leu Ser Asp
                20                  25                  30

His Pro Glu Leu Glu Gln Val Ile Trp Thr Leu Leu Gln His Thr Leu
            35                  40                  45

Gln Gln Glu Tyr Glu Leu Met Arg Asp Arg His Leu Asp Gln Ile Met
        50                  55                  60

Met Cys Ser Met Tyr Gly Ile Cys Lys Ala Lys Asn Ile Asp Leu Arg
 65                  70                  75                  80

Phe Lys Thr Ile Val Thr Ala Tyr Lys Gly Leu Thr Asn Thr Asn Gln
                85                  90                  95

Glu Thr Phe Lys His Val Leu Ile Arg Asp Gly Gln His Asp Ser Ile
            100                 105                 110

Ile Val Phe Tyr Asn Leu Val Phe Met Gln Lys Leu Lys Ser His Ile
        115                 120                 125

Leu

<210> SEQ ID NO 15
<211> LENGTH: 131
<212> TYPE: PRT
<213> ORGANISM: Gallus sp.

<400> SEQUENCE: 15

Gln Lys Pro Gln Lys Ser Thr Ser Leu Ser Leu Phe Tyr Lys Lys Val
 1               5                  10                  15

Phe Arg Leu Ala Tyr Leu Arg Leu His Thr Leu Phe Arg Leu Leu
                20                  25                  30

Ser Glu His Pro Asp Leu Glu Pro Leu Ile Trp Thr Leu Phe Gln His
            35                  40                  45

Thr Leu Gln Asn Glu Ser Glu Leu Met Arg Asp Arg His Leu Asp Gln
        50                  55                  60

Ile Met Met Cys Ser Met Tyr Gly Ile Cys Lys Val Lys Asn Val Asp
 65                  70                  75                  80

Leu Arg Phe Lys Thr Ile Val Ser Ala Tyr Lys Glu Leu Pro Asn Thr
                85                  90                  95

Asn Gln Glu Thr Phe Lys Arg Val Leu Ile Arg Glu Glu Gln Tyr Asp
            100                 105                 110

Ser Ile Ile Val Phe Tyr Asn Leu Val Phe Met Gln Lys Leu Lys Thr
        115                 120                 125

Asn Ile Leu
    130

<210> SEQ ID NO 16
<211> LENGTH: 131
<212> TYPE: PRT
<213> ORGANISM: Mus sp.

<400> SEQUENCE: 16

Gln Lys Pro Leu Lys Ser Thr Ser Leu Ala Leu Phe Tyr Lys Lys Val
 1               5                  10                  15

-continued

```
Tyr Arg Leu Ala Tyr Leu Arg Leu Asn Thr Leu Cys Ala Arg Leu Leu
             20                  25                  30

Ser Asp His Pro Glu Leu Glu His Ile Ile Trp Thr Leu Phe Gln His
         35                  40                  45

Thr Leu Gln Asn Glu Tyr Glu Leu Met Arg Asp Arg His Leu Asp Gln
     50                  55                  60

Ile Met Met Cys Ser Met Tyr Gly Ile Cys Lys Val Lys Asn Ile Asp
 65                  70                  75                  80

Leu Lys Phe Lys Ile Ile Val Thr Ala Tyr Lys Asp Leu Pro His Ala
                 85                  90                  95

Ala Gln Glu Thr Phe Lys Arg Val Leu Ile Arg Glu Glu Phe Asp
             100                 105                 110

Ser Ile Ile Val Phe Tyr Asn Ser Val Phe Met Gln Arg Leu Lys Thr
         115                 120                 125

Asn Ile Leu
     130

<210> SEQ ID NO 17
<211> LENGTH: 130
<212> TYPE: PRT
<213> ORGANISM: Homo sapiens

<400> SEQUENCE: 17

Gln Lys Pro Leu Lys Ser Thr Ser Leu Ser Leu Phe Tyr Lys Lys Val
  1               5                  10                  15

Tyr Arg Leu Ala Tyr Leu Arg Asn Thr Leu Cys Glu Arg Leu Leu Ser
             20                  25                  30

Glu His Pro Glu Leu Glu His Ile Ile Trp Thr Leu Phe Gln His Thr
         35                  40                  45

Leu Gln Asn Glu Tyr Glu Leu Met Arg Asp Ala His Leu Asp Gln Ile
     50                  55                  60

Met Met Cys Ser Met Tyr Gly Ile Cys Lys Val Lys Asn Ile Asp Leu
 65                  70                  75                  80

Lys Phe Lys Ile Ile Val Thr Ala Tyr Lys Asp Leu Pro His Ala Val
                 85                  90                  95

Gln Glu Thr Phe Lys Arg Val Leu Ile Lys Glu Glu Tyr Asp Ser
             100                 105                 110

Ile Ile Val Phe Tyr Asn Ser Val Phe Met Gln Arg Leu Lys Thr Asn
         115                 120                 125

Ile Leu
     130

<210> SEQ ID NO 18
<211> LENGTH: 166
<212> TYPE: PRT
<213> ORGANISM: Homo sapiens

<400> SEQUENCE: 18

Asn Arg Pro Lys Arg Thr Gly Ser Leu Ala Leu Phe Tyr Arg Lys Val
  1               5                  10                  15

Tyr His Leu Ala Ser Val Arg Leu Arg Asp Leu Cys Leu Lys Leu Asp
             20                  25                  30

Val Ser Asn Glu Leu Arg Arg Lys Ile Trp Thr Cys Phe Glu Phe Thr
         35                  40                  45

Leu Val His Cys Pro Asp Leu Met Lys Asp Arg His Leu Asp Gln Leu
     50                  55                  60
```

-continued

```
Leu Leu Cys Ala Phe Tyr Ile Met Ala Lys Val Thr Lys Glu Glu Arg
 65                  70                  75                  80

Thr Phe Gln Glu Ile Met Lys Ser Tyr Arg Asn Gln Pro Gln Ala Asn
                 85                  90                  95

Ser His Val Tyr Arg Ser Val Leu Leu Lys Ser Ile Pro Arg Glu Val
                100                 105                 110

Val Ala Tyr Asn Lys Asn Ile Asn Asp Asp Phe Glu Met Ile Asp Cys
            115                 120                 125

Asp Leu Glu Asp Ala Thr Lys Thr Pro Asp Cys Ser Ser Gly Pro Val
    130                 135                 140

Lys Glu Glu Arg Ser Asp Leu Ile Lys Phe Tyr Asn Thr Ile Tyr Gly
145                 150                 155                 160

Arg Val Ser Phe Ala Leu
                165
```

<210> SEQ ID NO 19
<211> LENGTH: 195
<212> TYPE: PRT
<213> ORGANISM: Homo sapiens

<400> SEQUENCE: 19

```
Asn Arg Pro Arg Lys Thr Ser Ser Leu Ser Leu Phe Phe Arg Lys Val
  1               5                  10                  15

Tyr His Leu Ala Ala Val Arg Leu Arg Asp Leu Cys Ala Lys Leu Asp
                 20                  25                  30

Ile Ser Asp Glu Leu Arg Lys Lys Ile Trp Thr Cys Phe Glu Phe Ser
             35                  40                  45

Ile Ile Gln Cys Pro Glu Leu Met Met Asp Arg His Leu Asp Gln Leu
 50                  55                  60

Leu Met Cys Ala Ile Tyr Val Met Ala Lys Val Thr Lys Glu Asp Lys
 65                  70                  75                  80

Ser Phe Gln Asn Ile Met Arg Cys Tyr Arg Thr Gln Pro Gln Ala Arg
                 85                  90                  95

Ser Gln Val Tyr Arg Ser Val Leu Ile Lys Gly Lys Arg Lys Arg Arg
                100                 105                 110

Asn Ser Gly Ser Ser Asp Ser Arg Ser His Gln Asn Ser Pro Thr Glu
            115                 120                 125

Leu Asn Lys Asp Arg Thr Ser Arg Asp Ser Ser Pro Val Met Arg Ser
    130                 135                 140

Ser Ser Thr Leu Pro Val Pro Gln Pro Ser Ser Ala Ala Pro Thr Pro
145                 150                 155                 160

Thr Arg Leu Thr Gly Ala Asn Ser Asp Met Glu Glu Glu Glu Arg Gly
                165                 170                 175

Asp Leu Ile Gln Phe Tyr Asn Asn Ile Tyr Ile Lys Gln Ile Lys Thr
            180                 185                 190

Phe Ala Met
        195
```